United States Patent [19]

Palazzotto

[11] Patent Number: 4,733,109

[45] Date of Patent: Mar. 22, 1988

[54] SECOND HARMONIC GENERATION WITH SCHIFF BASES

[75] Inventor: Michael C. Palazzotto, St. Paul, Minn.

[73] Assignee: Minnesota Mining and Manufacturing Company, St. Paul, Minn.

[21] Appl. No.: 825,469

[22] Filed: Feb. 3, 1986

[51] Int. Cl.$^4$ .............................................. H03F 7/00
[52] U.S. Cl. ................................. 307/427; 252/299.5; 252/299.68
[58] Field of Search ................... 372/21, 22; 307/427; 252/299.65, 299.5, 299.68

[56] References Cited

U.S. PATENT DOCUMENTS

| | | | |
|---|---|---|---|
| 3,395,329 | 7/1968 | Rentzepis | 321/69 |
| 3,431,484 | 3/1969 | Pao et al. | 321/69 |
| 3,827,780 | 8/1974 | Labes | 350/160 LC |
| 3,858,124 | 12/1974 | Bass et al. | 332/7.51 |
| 4,031,028 | 6/1977 | Maze | 252/299.65 |
| 4,047,803 | 9/1977 | Yaguchi et al. | 350/160 LC |
| 4,058,477 | 11/1977 | Boller et al. | 252/299 |
| 4,125,534 | 11/1978 | Yee | 260/315 |
| 4,173,544 | 11/1979 | Osman | 252/299 |
| 4,199,698 | 4/1980 | Betha et al. | 307/425 |
| 4,376,899 | 3/1983 | Chemla et al. | 307/425 |
| 4,431,263 | 2/1984 | Garito | 350/96.34 |

OTHER PUBLICATIONS

Kurtz et al, "A Powder Technique for the Evaluation of Nonlinear Optical Materials", *Journal of Applied Physics*, vol. 39, No. 8, Jul. 1968, pp. 3798–3813.

Filipenko et al, "Crystal Structure and Nonlinear Optical Properties of Monoclinic p-nitro-p'-methylbenzylideneaniline", *Sov. Phys.* Crystallogr., vol. 22, No. 3 (1977), pp. 305–310.

Williams, Organic Polymeric and Non-Polymeric Materials with Large Optical Nonlinearities", *Angelu. Chem. Int. Ed. Engl.* 23, (1984), pp. 690–703.

*Primary Examiner*—James W. Davie
*Attorney, Agent, or Firm*—Donald M. Sell; James A. Smith; David L. Weinstein

[57] ABSTRACT

Devices for and method of generating coherent second harmonic light radiation. The devices comprise a laser source of coherent light radiation at a fixed fundamental frequency, a Schiff base compound, means for directing the output radiation of the laser onto the Schiff base compound, and output means for utilizing the second harmonic frequency. Preferably, one moiety of the Schiff base compound has a hyperpolarizable group and the other moiety of the Schiff base compound has a configuration so that the compound crystallizes in a non-centrosymmetric configuration.

28 Claims, 1 Drawing Figure

SECOND HARMONIC GENERATION WITH SCHIFF BASES

TECHNICAL FIELD

This invention is concerned with materials for nonlinear optical devices for the conversion of optical energy at one frequency to optical energy at another frequency.

BACKGROUND OF THE INVENTION

Laser techniques have been developed to a great extent and it is possible at present to obtain various kinds or types of laser light by utilizing solid, gas, and liquid media. In many purposes of applications utilizing coherent laser light, laser light having various wavelengths is required and in some cases, a laser light exhibiting a continuous spectrum over a certain range of wavelengths is required. However, it is difficult to satisfy the aforesaid purposes or requirements even with the various kinds of laser light obtainable at present. Hence, a means has frequently been employed in which coherent laser light is converted into laser light of the second harmonic; that is to say, laser light of a wavelength of which the frequency is obtained is twice the fundamental frequency, by passing the laser light through a nonlinear optical crystal. Conversion of the wavelength of a laser light by a parametric effect using such a nonlinear optical crystal has also been investigated and developed.

In the prior art, monocrystalline forms of potassium dihydrogen phosphate (KDP), ammonium dihydrogen phosphate (ADP), barium sodium niobate (BaNaNbO$_3$), and lithium niobate (LiNbO$_3$) were used as coherent light phase modulators and for generating higher frequency harmonics. Monocrystalline KDP and ADP, while offering greater resistance to optical irradiation induced surface damage due to laser beam bombardment, do not exhibit large optical nonlinearities. This rendered these crystals unsuitable for higher harmonic frequency generation or conversion. In contrast, BaNaNbO$_3$ and LiNbO$_3$ showed large nonlinearities but, unfortunately, a low resistance to optical damage. In this regard, the term "resistance to optical damage" means the number of times the surface of a crystalline material can be bombarded (shots) with laser radiation of a given power density in watts per unit area before the subject crystal shows signs of opacity. Thus, a crystal showing high resistance would require a larger number of shots than a crystal of low resistance for the same power density of the incident laser beams.

All of the above-mentioned crystals vary their refractive index when an electric field is applied to them. Thus, such crystals find employment as electro-optic phase modulators. While these crystals can be used both in the form of powdered samples and large single crystals, it has been recognized that large single crystals are preferred because large electro-optical and nonlinear effects can be obtained through their use.

The possibility of using organic molecules in nonlinear optical devices has generated much interest recently because a large number of molecules are available for investigaton. Some substituted aromatic molecules are known to exhibit large optical nonlinearities. The possibility of such an aromatic molecule having large optical nonlinearities is enhanced if the molecule has donor and acceptor groups bonded at opposite ends of the conjugated system of the molecule.

U.S. Pat. No. 4,199,698 discloses that the nonlinear optical properties of 2-methyl-4-nitroaniline (MNA) make it a highly useful material in nonlinear devices that convert coherent optical radiation including a first frequency into coherent optical radiation including a second frequency. The nonlinear devices have means for introducin coherent radiation of a first frequency into the MNA and means for utilizing coherent radiation emitted from the MNA at a second frequency.

U.S. Pat. No. 4,431,263 discloses that diacetylenes and polymers formed form diacetylenic species, which are amendable to close geometric, steric, structural, and electronic control, provide nonlinear optic, waveguide, piezoelectric, and pyroelectric materials and devices. Diacetylenes which are crystallizable into crystals having a noncentrosymmetric unit cell may form single crystals or be elaborated into a thin film upon a substrate by the Langmuir-Blodgett technique. Such films may be polymerized either thermally or by irradiation for use in nonlinear optical and other systems. Diacetylenes are covalently bonded to substrates through the employment of silane species and subsequently polymerized to yield nonlinear optic and other devices having high structural integrity in addition to high efficiencies and optical effects.

Sov. Phys. Crystallogr. 22, 305 (1977) discloses that a compound having the structure exhibits second harmonic generation. However, this paper does not suggest or predict that Schiff base compounds in general will exhibit second harmonic generation. Isomers of the aforementioned compound, e.g.

pack in a centrosymmetric space group, and, consequently, observation of second harmonic generation is eliminated.

SUMMARY OF THE INVENTION

In one aspect this invention involves generation of coherent second harmonic light radiation by devices that incorporate certain Schiff base compounds therein. In another aspect, this invention involves a method of generating coherent second harmonic light radiation by the aforementioned devices. In a third aspect, several of the Schiff base compounds found to be useful in the devices described herein are novel per se, i.e. they are not known to ever have been previously prepared.

In general, second harmonic generators of this invention comprise, in combination, a laser source of coherent light radiation at a fixed fundamental frequency, an organic molecular crystalline compound selected from particular classes of Schiff base compounds, means for directing the output radiation of the laser onto the organic molecular crystalline Schiff base compound, and output means for utilizing the second harmonic frequency.

Schiff base compounds that can be used in the present invention are defined as those Schiff base compounds which crystallize in a non-centrosymmetric configuration and which contain a moiety selected from the group consisting of (a) 4-dialkylaminophenyl methylene amino, (b) 2-hydroxyphenyl methylene amino, and (c) 4-hydroxyphenyl methylene amino.

The following four classes of Schiff base compounds are preferred for use in devices for generation of coherent second harmonic light radiation:

(I) Compounds containing 4-dialkylaminophenyl methylene amino moiety bonded to a substituted phenyl moiety, wherein the substituent or substituents on the phenyl moiety is selected so that the Schiff base compound crystallizes in a non-centrosymmetric configuration;

(II) Compounds containing 4-dialkylaminophenyl methylene amino moiety bonded to a second moiety selected such that the Schiff base compound is optically active, such as, for example, wherein the second moiety contains an asymmetric carbon atom;

(III) Compounds containing 2-hydroxyphenyl methylene amino moiety bonded to a moiety which renders the compound capable of being a photochromic material;

(IV) Compounds containing 4-hydroxyphenyl methylene amino moiety bonded to an unsubstituted or substituted 4-nitrophenyl moiety, wherein any substituent or substituents on the 4-nitrophenyl moiety, if any, is selected so that the Schiff base compound crystallizes in a non-centrosymmetric configuration.

In general, it is preferred that one moiety of the Schiff base compound have a hyperpolarizable group and the other moiety of the Schiff base compound have a configuration which provides that the resultant compound crystallizes in a non-centrosymmetric configuration.

The Schiff base compounds of the present invention are useful for providing second order optical effects. These compounds can be incorporated in devices known to be useful as second harmonic generators.

DETAILED DESCRIPTION

All Schiff base compounds are characterized by the anil linkage,

Schiff base compounds that have been found to exhibit second harmonic generation are crystalline in form, and are preferably in solid crystalline form. While Schiff base compounds in liquid crystalline form may also exhibit second harmonic generation, detection of signals from Schiff base compounds in liquid crystalline form is difficult. Regardless of whether they are in solid crystalline form or in liquid crystalline form, Schiff base compounds suitable for this invention must have a non-centrosymmetric configuration. Non-centrosymmetric species are those which have no center of symmetry on either the molecular or crystalline unit cell level.

Schiff base compounds suitable for this invention must be sufficiently transparent to incident electromagnetic radiation in the specified range so that the efficiency of second harmonic generation (SHG) can be detected by conventional SHG detection devices. For example, where the wavelength of incident radiation is 1.064 $\mu$m, and the wavelength of the generated second harmonic is 0.532 $\mu$m, the Schiff base compound must allow sufficient radiation to pass at both wavelengths to detect at least one photon of 0.532 $\mu$m wavelength light.

Schiff base compounds that have been found to be preferable for this invention can be represented by the following general formulas:

wherein $R^1$ represents a member selected from the group consisting of chloro, bromo, iodo, cyano, lower alkoxy, and lower alkylthio, and

$R^2$ represents a member selected from the group consisting of halo, cyano, lower alkoxy, lower alkylthio, and hydrogen, provided that $R^1$ is not the same as $R^2$;

wherein

$R^3$ represents a group which renders the molecule optically active, and $R^4$ represents a member selected from the group consisting of dimethylamino and diethylamino;

wherein $R^5$ represents a group which renders the molecule capable of being a photochromic material, e.g. alkylphenyl, halophenyl, cyanophenyl, nitrophenyl;

wherein $R^6$ represents a member selected from the group consisting of hydrogen, lower alkoxy, lower alkyl, lower alkylthio, cyano, and halo.

As used herein, "photochromic materials" are materials which change their color as a result of absorption of electromagnetic energy. Photochromism is discussed in Kirk-Othmer Encyclopedia of Chemical Technology, Third Edition, Vol. 6, John Wiley & Sons (New York: 1984) pp. 121-128. See also J. Chem. Soc. 2041 (1964). "Optically active" means that characteristic of a substance which renders it capable of rotating the plane of vibration of polarized light to the left or right. See Hackh's Chemical Dictionary, Fourth Edition, McGraw-Hill, Inc. (New York, 1972). "Lower alkoxy" means alkoxy group having 1 to 4 carbon atoms; "lower alkylthio" means alkylthio group having 1 to 4 carbon atoms; "lower alkyl" means alkyl group having 1 to 4 carbon atoms; "halo" means the group consisting of fluoro, chloro, bromo, and iodo.

In structural formula II, $R^3$ is preferably a group of the structure wherein

C* represents an asymmetric carbon atom that is bonded to the nitrogen atom of the anil linkage of the Schiff base compound, and $R^a$, $R^b$, and $R^c$ independently represent a member of the group selected from hydrogen, alkyl, aryl, aralkyl, alkaryl, provided that $R^a$, $R^b$, and $R^c$ are all different. Preferably $R^a$ represents unsubstituted or substituted phenyl group, $R^b$ represents unsubstituted or substituted alkyl group, and $R^c$ represents hydrogen atom. The particular substituents on $R^a$ and $R^b$ should be selected so that the Schiff base molecule is optically active. Other than this requirement, the character of the substituents is not critical. It should also be noted that if the R-isomer of the Schiff base provides a non-zero value of SHG efficiency, the S-isomer of the Schiff base will also provide a non-zero value for SHG efficiency.

While many of the Schiff base compounds represented by the aforementioned structural formulas are known, several, including some of those exhibiting the highest values of SHG efficiency, have never before been reported. These novel Schiff base compounds can be represented by the following formulas:

Ia wherein $R^1$ represents a member selected from the group consisting of chloro, bromo, iodo, cyano, lower alkoxy, and lower alkylthio, and $R^2$ represents a member selected from the group consisting of halo, cyano, lower alkoxy, and lower alkylthio, provided that $R^1$ is not the same as $R^2$;

IVa wherein $R^6$ represents a member selected from the group consisting of hydrogen, lower alkoxy, lower alkyl, lower alkylthio, cyano, and halo.

It has been found that, in general, substitution of a bulky, electron-rich substituent in the ortho-position (2-position) on the N-phenyl ring of a Schiff base compound (i.e., the phenyl moiety bonded to the nitrogen atom of the anil linkage) provides a Schiff base compound that exhibits efficient second harmonic generation. Additionally, the further substitution of a second bulky, electron-rich substituent in the 5-position on the N-phenyl ring of a Schiff base compound provides improvement in second harmonic generation efficiency.

Methods of preparing Schiff base compounds are well known. They can be readily prepared by condensation of an aldehyde or ketone with an appropriate amine under a variety of conditions.

The reactants can simply be introduced into a monohydric alcohol solvent, e.g. methanol, ethanol, and allowed to react in the presence of, or absence of, external heat. Alternatively, the reactants can be introduced into a non-alcoholic solvent, e.g. toluene, and allowed to react in the presence of, or absence of external heat. Water generated by the reaction can be removed preferably by means of absorption by molecular sieves. According to a different procedure, the reactants can be introduced into toluene, heated, and the water removed therefrom by means of a Dean-Stark trap. A catalyst, e.g. p-toluenesulfonic acid, can be employed, but is not required.

The Schiff base reaction product can be purified by recrystallization from solvents, e.g. ethanol, methanol, acetone, acetonitrile, methylethyl ketone, acetone/hexane, acetone/isopropanol, methylene chloride/heptane. Selection of the optimum solvent is well-known to those of ordinary skill in the art.

The aforementioned Schiff base compounds are substantially transparent to electromagnetic radiation having wavelengths from 400-500 nm to 1064 nm. Accordingly, they are useful in second harmonic generators wherein both incident radiation and emergent radiation range from 400 nm to 1064 nm.

Devices that are capable of generating coherent second harmonic light radiation with the Schiff bases described herein are well known in the art. Representative examples of such devices are described in U.S. Pat. Nos. 3,395,329, 3,431,484, and 3,858,124, all of which are incorporated herein by reference for the purpose of describing devices which can incorporate the Schiff bases described herein and exhibit efficient second harmonic generation by means of such incorporation.

Schiff base crystals were evaluated for SHG efficiency using the SHG powder test described in Kurtz et al., J. Appl. Phys. 39, 3798, 1968. Each Schiff base was ground and sieved and then mixed with a fluid, i.e., a liquid, to minimize refraction caused by differences in the index of refraction between the particles and the ambient atmosphere. The index-matched sample was placed between cell flats spaced 0.2 mm apart. Particles having mean diameter greater than 90 μm but less than 180 μm were used. Each sample was mixed with a drop of index matching fluid (Cargille n=1.63 or n=1.58 fluids or n=1.631 Convalex oil). The samples were not indexed matched critically, so that the actual SHG efficiencies reported in the examples may be higher.

Figure 1:
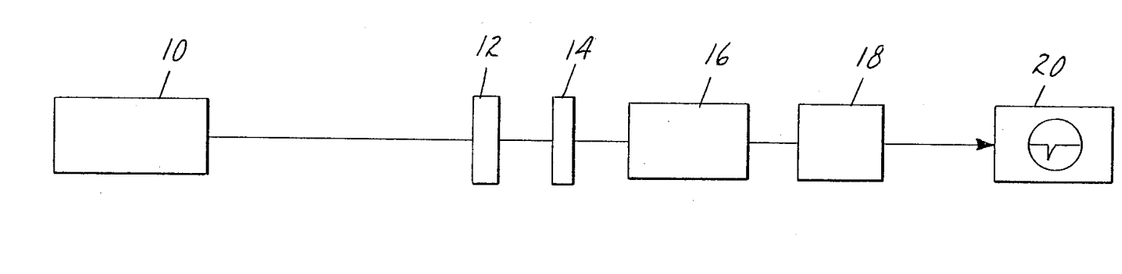
The drawing is a diagrammatic presentation of a suitable arrangement for demonstrating the second harmonic generating properties of the Schiff bases of this invention.

Referring now to FIG. 1, infrared radiation at 1064 nm from a Q-switched Nd-YAG laser 10 was weakly focused onto the cell 12 containing the prepared sample. In the device illustrated in FIG. 1, the means for directing the output radiation of the laser, e.g. a lens, onto the cell 12 containing the Schiff base sample is integrated into the laser 10 and is not shown as a separate component. Means for directing the output radiation of the laser onto the organic molecular crystalline compound are well-known to one of ordinary skill in the art. An infrared blocking filter 14 placed behind the sample allowed only the second harmonic frequency or frequency-doubled radiation to pass through a ⅓ meter monochrometer 16 tuned at 532 nm. The output of the monochrometer 16 was directed to a cooled photomultiplier tube 18, and the resulting signal was processed by a boxcar averager 20 that averages over many laser pulses. Urea was the chosen standard because of its high second order coefficient and its ready availability. The urea standard was prepared in the same manner as the samples. The urea standard was indexed matched reasonably well, with a mismatch of about 0.01. The reported efficiency of a sample is its SHG signal normalized to that of the urea standard measured under the same experimental conditions.

The following examples are meant to illustrate, but not limit this invention. Parts and percentages are by weight unless otherwise indicated. All of the compounds prepared in the examples and comparative examples were characterized by standard analytical techniques, e.g. infrared spectroscopy, ultraviolet/visible absorption spectroscopy, nuclear magnetic resonance spectroscopy, melting point, and elemental analysis.

EXAMPLE 1

Equimolar amounts of the reactants o-cyanoaniline (0.042 mole) and p-dimethylaminobenzaldehyde (0.042 mole) were added to 150 ml toluene containing 50 ml molecular sieves in a 250-ml Erlenmeyer flask. Water of reaction was removed by absorption by the molecular sieves. The reaction mixture was stirred over the molecular sieves at room temperature (20° C.) for 72 hours. The resulting solution was filtered, the toluene filtrate saved, and the molecular sieves extracted with methylene chloride. The methylene chloride extract was combined with the toluene filtrate, and the solvent removed therefrom under reduced pressure to provide a residue which was recrystallized from a solvent mixture comprising methylene chloride and heptane. The yield was approximately 33%. The resulting product was 2-[{(4-dimethylaminophenyl)methylene}amino]cyanobenzene. This compound exhibited an SHG efficiency of 2.30.

EXAMPLES 2-5

Preparation the Schiff base compounds listed in Table I below was accomplished by the procedure described in Example 1 above, i.e. equimolar amounts of the amine and aldehyde were reacted together and the resulting product recovered according to the described procedure.

TABLE I

| Example | Aldehyde | Amine | Schiff base | SHG efficiency |
|---|---|---|---|---|
| 2 | p-dimethylaminobenzaldehyde | o-bromoaniline | 2-[{(4-dimethylaminophenyl)methylene}amino]-bromobenzene | 1.87 |
| 3 | p-dimethylaminobenzaldehyde | o-iodoaniline | 2-[{(4-dimethylaminophenyl)methylene}amino]-iodobenzene | 0.016 |
| 4 | p-dimethylaminobenzaldehyde | o-methoxyaniline | 2-[{(4-dimethylaminophenyl)methylene}amino]-methoxybenzene | 2.3 |
| 5 | p-dimethylaminobenzaldehyde | 2-methoxy-5-chloroaniline | 2-[{(4-dimethylaminophenyl)methylene}amino]-4-chloro-methoxybenzene | 28.5 |

COMPARATIVE EXAMPLES A-F

Preparation of the Schiff base compounds listed in Table II below was accomplished by the procedure described in Example 1 above, i.e. equimolar amounts of the amine and aldehyde were reacted together and the resulting product recovered according to the described procedure.

TABLE II

| Example | Aldehyde | Amine | Schiff base | SHG efficiency |
|---|---|---|---|---|
| A | p-dimethylaminobenzaldehyde | o-fluoroaniline | 2-[{(4-dimethylaminophenyl)methylene}amino]-fluorobenzene | 0.001 |
| B | p-dimethylaminobenzaldehyde | 2-methoxy-5-methylaniline | 2-[{(4-dimethylaminophenyl)methylene}amino]-4-methyl-methoxybenzene | 0.0 |
| C | p-dimethylaminobenzaldehyde | 2-methoxy-5-nitroaniline | 2-[{(4-dimethylaminophenyl)methylene}amino]-4-nitro-methoxybenzene | 0.0 |
| D | p-dimethylaminobenzaldehyde | 2,4-dibromoaniline | 1-[{(4-dimethylaminophenyl)methylene}amino]-2,4-dibromobenzene | 0.0 |
| E | p-dimethylaminobenzaldehyde | 2,4-dichloroaniline | 1-[{(4-dimethylaminophenyl)methylene}amino]-2,4-dichlorobenzene | 0.0 |
| F | p-dimethylaminobenzaldehyde | m-cyanoaniline | 3-[{(4-dimethylaminophenyl)methylene}amino]-cyanobenzene | 0.0 |

EXAMPLE 6

Equimolar amounts of the reactants, R-(+)-α-methylbenzylamine (0.077 mole) and salicylaldehyde (0.077 mole), were mixed in 50 ml ethanol, and the mixture stirred and heated for about 2 hours to insure the completion of the reaction. The mixture was then allowed to cool to room temperature (20° C.). The product, which crystallized upon cooling, was isolated by filtration. The yield was approximately 67%. The resulting product was R-1-[{(2-hydroxyphenyl)methylene}amino]-1-phenylethane. This Compound exhibited an SHG efficiency of 0.18.

EXAMPLE 7-10

Preparation of the Schiff base compounds listed in Table III below was accomplished by the procedure described in Example 6 above, i.e. equimolar amounts of the amine and aldehyde were reacted together and the resulting product recovered according to the described procedure.

EXAMPLE 11

Equimolar amounts of the reactants, o-chloroaniline (0.09 mole) and p-dimethylaminobenzaldehyde (0.09 mole), were dissolved in 200 ml toluene in a 500 ml round-bottomed flask fitted with a condenser and Dean-Stark trap for separating and collecting water generated by the reaction. The reaction mixture was heated to reflux and the water collected. The reaction was alowed to proceed until close to the theoretical amount of water had been collected. The amount of time required varied from 12 to 24 hours. The solvent was removed under reduced pressure and the residue was recrystallized from a solvent mixture comprising methylene chloride and heptane. The yield was approximately 60%. The resulting product was 2-[{(4-dime-

TABLE III

| Example | Aldehyde | Amine | Schiff base | SHG efficiency |
|---|---|---|---|---|
| 7 | Salicylaldehyde | aniline | [{(2-hydroxyphenyl)methylene}amino]-benzene | 0.21 |
| 8 | Salicylaldehyde | m-bromoaniline | 3-[{(2-hydroxyphenyl)methylene}amino]-bromobenzene | 0.16 |
| 9 | Salicylaldehyde | p-bromoaniline | 4-[{(2-hydroxyphenyl)methylene}amino]-bromobenzene | 0.016 |
| 10 | p-dimethylaminobenzaldehyde | R—(+)-α-methylbenzylamine | R—1-[{(4-dimethylaminophenyl)methylene}amino]-1-phenylethane | 0.97 |

COMPARATIVE EXAMPLES G-K

Preparation of the Schiff base compounds listed in Table IV below was accomplished by the procedure described in Example 6 above, i.e. equimolar amounts of the amine and aldehyde were reacted together and the resulting product recovered according to the described procedure.

thylaminophenyl)methylene}amino]-chlorobenzene. This compound had an SHG efficiency of 0.67.

COMPARATIVE EXAMPLES L-S

Preparation of the Schiff base compounds listed in Table V below was accomplished by the procedure described in Example 11 above, i.e. equimolar amounts of the amine and aldehyde were reacted together and

TABLE IV

| Example | Aldehyde | Amine | Schiff base | SHG efficiency |
|---|---|---|---|---|
| G | p-dimethylaminobenzaldehyde | p-chloroaniline | 4-[{(4-dimethylaminophenyl)methylene}amino]-chlorobenzene | 0.0 |
| H | p-dimethylaminobenzaldehyde | p-bromoaniline | 4-[{(4-dimethylaminophenyl)methylene}amino]-bromobenzene | 0.01 |
| I | p-dimethylaminobenzaldehyde | p-cyanoaniline | 4-[{(4-dimethylaminophenyl)methylene}amino]-cyanobenzene | 0.0 |
| J | p-dimethylaminobenzaldehyde | p-methoxyaniline | 4-[{(4-dimethylaminophenyl)methylene}amino]-methoxybenzene | 0.0 |
| K | p-dimethylaminobenzaldehyde | aniline | [{(4-dimethylaminophenyl)methylene}amino]-benzene | 0.0 | the resulting product recovered according to the described procedure.

TABLE V

| Example | Aldehyde | Amine | Schiff base | SHG efficiency |
|---|---|---|---|---|
| L | p-nitrobenzaldehyde | o-methoxyaniline | 2-[{(4-nitrophenyl)methylene}amino]-methoxybenzene[a] | 0.0 |
| M | p-naphthaldehyde | o-methoxyaniline | 2-[{(2-naphthyl)methylene}amino]-methoxybenzene[b] | 0.002 |
| N | p-chlorobenzaldehyde | o-methoxyaniline | 2-[{(4-chlorophenyl)methylene}amino]-methoxybenzene | 0.0 |
| O | p-dimethylaminobenzaldehyde | o-methylaniline | 2-[{(4-dimethylaminophenyl)methylene}amino]-methylbenzene | 0.0 |
| P | p-dimethylaminobenzaldehyde | o-ethylaniline | 2-[{(4-dimethylaminophenyl)methylene}amino]-ethylbenzene | 0.0 |
| Q | p-dimethylaminobenzaldehyde | m-methoxyaniline | 3-[{(4-dimethylaminophenyl)methylene}amino]-methoxybenzene | 0.0 |
| R | p-dimethylaminobenzaldehyde | m-bromoaniline | 3-[{(4-dimethylaminophenyl)methylene}amino]-bromobenzene | 0.0 |
| S | p-diethylaminobenzaldehyde | 2-methoxy-5- | 2-[{(4-diethylaminophenyl)methylene}amino]- | 0.0 |

TABLE V-continued

| Example | Aldehyde | Amine | Schiff base | SHG efficiency |
|---|---|---|---|---|
| | | chloroanilne | 4-chloro-methoxybenzene | |

[a] Schiff base compound was recrystallized from a mixture of acetone and ethanol.
[b] Schiff base compound was recrystallized from a mixture of methylene chloride and hexane.

EXAMPLE 12

Equimolar amounts of the reactants, 2-methoxy-5-bromoaniline (0.025 mole) and p-dimethylaminobenzaldehyde (0.25 mole) were dissolved in 200 ml toluene in a 500-ml round-bottomed flask fitted with a condenser and containing 50 ml of molecular sieves. The mixture was refluxed for 8 hours, then allowed to cool to room temperature (20° C.). The solution was filtered, the toluene filtrate saved, and the molecular sieves extracted with methylene chloride. The methylene chloride washings were combined with the toluene, and the solvent was removed under reduced pressure. The residue obtained was recrystallized from a solvent mixture comprising methylene chloride and heptane. The yield was approximately 60%. The resulting product was 2-[{(4-dimethylaminophenyl)methylene}amino]-4-bromomethoxybenzene. This compound had an SHG efficiency of 2.9.

EXAMPLES 13-17

Preparation of the Schiff base compounds listed in Table VI below was accomplished by the procedure described in Example 12 above, i.e. equimolar amounts of the amine and aldehyde were reacted together and the resulting product recovered according to the described procedure.

TABLE VII

| Example | Aldehyde | Amine | Schiff base | SHG efficiency |
|---|---|---|---|---|
| T | p-dimethylaminobenzaldehyde | 2,5-dibromoaniline | 1-[{(4-dimethylaminophenyl)methylene}amino]-2,5-dibromobenzene | 0.04 |
| U | p-dimethylaminobenzaldehyde | m-methylthioaniline | 3-[{(4-dimethylaminophenyl)methylene}amino]-methylthiobenzene | 0.0 |
| V | p-dimethylaminobenzaldehyde | 2-methyl-5-chloroaniline | 2-[{(4-dimethylaminophenyl)methylene}amino]-4-chloro-methylbenzene | 0.0 |
| W | p-dimethylaminobenzaldehyde | 2,5-dichloroaniline | 1-[{(4-dimethylaminophenyl)methylene}amino]-2,5-dichlorobenzene | 0.0 |
| X | p-dimethylaminobenzaldehyde | 2-methoxy-4-bromoaniline | 2-[{(4-dimethylaminophenyl)methylene}amino]-5-bromomethoxybenzene | 0.0 |
| Y | m-hydroxybenzaldehyde | p-nitroaniline | 4-[{(3-hydroxyphenyl)methylene}amino]-nitrobenzene[a] | 0.0 |

[a] Schiff base was recrystallized from a mixture of N,N—dimethylformamide and water.

From observation of the results of the examples and comparative examples, it has been found that Schiff base compounds derived from p-dimethylaminobenzaldehyde, p-diethylaminobenzadehyde, o-hydroxybenzaldehyde, or p-hydroxybenzaldehyde provide SHG efficiency values above zero.

From observations of the results of the examples and comparative examples, it can be seen that not all Schiff base compounds exhibit positive values of SHG efficiency. For example, in comparing Example 4 with Comparative Examples Q and J, it can be seen that when the methoxy group is in the 2-position (Example 4), the value of SHG efficiency is positive, but when the methoxy group is in the 3-position (Comparative Example Q) or 4-position (Comparative Example J), the values of SHG efficiency is zero.

Various modifications and alterations of this invention will become apparent to those skilled in the art without departing from the scope and spirit of this invention is not to be unduly limited to the illustrative embodiments set forth herein.

What is claimed is:

1. A second harmonic generator comprising, in combination, a laser source of coherent light radiation at a fixed fundamental frequency, an organic molecular crystalline compound, means for directing the output radiation of the laser onto the compound, and output

TABLE VI

| Example | Aldehyde | Amine | Schiff base | SHG efficiency |
|---|---|---|---|---|
| 13 | p-dimethylaminobenzaldehyde | o-methylthio-aniline | 2-[{(4-dimethylaminophenyl)methylene}amino]-methylthiobenzene | 0.7 |
| 14 | p-diethylaminobenzaldehyde | (R)—(+)-α-methyl-benzylamine | R—1-[{(4-diethylaminophenyl)methylene}amino]-1-phenylethane | 4.9 |
| 15 | p-hydroxybenzaldehyde | p-nitroaniline | 4-[{(4-hydroxyphenyl)methylene}amino]-nitrobenzene[a] | 1.6 |
| 16 | p-hydroxybenzaldehyde | 2-methoxy-4-nitroaniline | 3-methoxy-4-[{(4-hydroxyphenyl)methylene}amino]nitrobenzene[a] | 10.7 |
| 17 | p-hydroxybenzaldehyde | 2-methyl-4-nitroaniline | 3-methyl-4-[{(4-hydroxyphenyl)methylene}-amino]nitrobenzene[a] | 0.3 |

[a] Molecular sieves were extracted with N,N—dimethylformamide and the Schiff base compound was recrystallized from a mixture of N,N—dimethylformamide and water.

COMPARATIVE EXAMPLES T-Y

Preparation of the Schiff base compounds listed in Table VI below was accomplished by the procedure described in Example 12 above, i.e. equimolar amounts means for utilizing the second harmonic frequency, said compound being a Schiff base which crystallizes in a non-centrosymmetric configuration and which contains a moiety selected from the group consisting of (a) 4-dialkylaminophenyl methylene amino, (b) 2-hydroxyphenyl methylene amino, and (c) 4-hydroxyphenyl methylene amino, said compound being transparent to radiation at said fixed fundamental frequency and said second harmonic frequency.

2. The second harmonic generator of claim 1 wherein said organic molecular crystalline compound is selected from the group consisting of
   (I) Schiff base compounds containing 4-dialkylaminophenyl methylene amino moiety bonded to a substituted phenyl moiety, wherein any substituent or substituents on the phenyl moiety is selected so that the Schiff base compound crystallizes in a non-centrosymmetric configuration;
   (II) Schiff base compounds containing 4-dialkylaminophenyl methylene amino moiety bonded to a second moiety such that the Schiff base compound is optically active;
   (III) Schiff base compounds containing 2-hydroxyphenyl methylene amino moiety bonded to a moiety which renders the compound capable of being a photochromic material; and
   (IV) Schiff base compounds containing 4-hydroxyphenyl methylene amino moiety bonded to an unsubstituted or substituted 4-nitrophenyl moiety, wherein any substituent or substituents on the 4-nitrophenyl moiety, if any, is selected so that the Schiff base compound crystallizes in a non-centrosymmetric configuration.

3. The second harmonic generator of claim 1 wherein the laser is a Nd-YAG laser.

4. The second harmonic generator of claim 1 wherein said compound is a solid.

5. A second harmonic generator comprising, in combination, a laser source of coherent light radiation at a fixed fundamental frequency, an organic molecular crystalline compound, means for directing the output radiation of the laser onto the compound, and output means for utilizing the second harmonic frequency, said compound being a Schiff base selected from the group consisting of wherein
   $R^1$ represents a member selected from the group consisting of chloro, bromo, iodo, cyano, lower alkoxy, lower alkylthio, and
   $R^2$ represents a member selected from the group consisting of halo, cyano, lower alkoxy, lower alkylthio, and hydrogen, provided that $R^1$ is not the same as $R^2$;

wherein
   $R^3$ represents a group which renders the molecule optically active, and
   $R^4$ represents a member selected from the group consisting of dimethylamino and diethylamino;

wherein
   $R^5$ represents a group which renders the molecule capable of being a photochromic material;

wherein
   $R^6$ represents a member selected from the group consisting of hydrogen, lower alkoxy, lower alkyl, lower alkylthio, cyano, and halo,
said compound being transparent to radiation at said fixed fundamental frequency and said second harmonic frequency.

6. The second harmonic generator of claim 5 wherein the compound is wherein
   $R^1$ represents a member selected from the group consisting of chloro, bromo, iodo, cyano, lower alkoxy, and lower alkylthio, and
   $R^2$ represents a member selected from the group consisting of halo, cyano, lower alkoxy, lower alkylthio, and hydrogen, provided that $R^1$ is not the same as $R^2$.

7. The second harmonic generator of claim 6 wherein the compound is 2-[{(4-dimethylaminophenyl)methylenene}amino]-4-chloro-methoxybenzene.

8. The second harmonic generator of claim 6 wherein the compound is 2-[{(4-dimethylaminophenyl)methylene}amino]-4-bromo-methoxybenzene.

9. The second harmonic generator of claim 5 wherein the compound is wherein
R³ represents a group which renders the molecule optically active, and
R⁴ represents a member selected from the group consisting of dimethylamino and diethylamino.

10. The second harmonic generator of claim 9 wherein the compound is R-1-[{(4-diethylaminophenyl)methylene}amino]-1-phenylethane.

11. The second harmonic generator of claim 9 wherein the compound is S-1-[{(4-diethylaminophenyl)methylene}amino]-1-phenylethane.

12. The second harmonic generator of claim 5 wherein the compound is wherein
R⁵ represents a group which renders the molecule capable of being a photochromic material.

13. The second harmonic generator of claim 12 wherein the compound is [{(2-hydroxyphenyl)methylene]-amino]benzene.

14. The second harmonic generator of claim 5 wherein the compound is wherein
R⁶ represents a member selected from the group consisting of hydrogen, lower alkoxy, lower alkyl, lower alkylthio, cyano, and halo.

15. The second harmonic generator of claim 14 wherein the compound is 3-methoxy-4-[{(4-hydroxyphenyl)methylene}-amino]nitrobenzene.

16. A process for converting a fixed fundamental frequency of coherent laser light into a second harmonic frequency which comprises passing said laser light through a nonlinear optical element comprising an organic molecular crystalline compound, said compound being a Schiff base which crystallizes in a non-centrosymmetric configuration and which contains a moiety selected from the group consisting of (a) 4-dialkylaminophenyl methylene amino, (b) 2-hydroxyphenyl methylene amino, and (c) 4-hydroxyphenyl methyl amino, said compound being transparent to said fixed fundamental frequency and to said second harmonic frequency.

17. The process of claim 16 wherein said organic molecular crystalline compound is selected from the group consisting of
(I) Schiff base compounds containing 4-dialkylaminophenyl methylene amino moiety bonded to a substituted phenyl moiety, wherein any substituent of the phenyl moiety is selected so that the Schiff base compound crystallizes in a non-centrosymmetric configuration;
(II) Schiff base compounds containing 4-dialkylaminophenyl methylene amino moiety bonded to a second moiety such that the Schiff base compound is optically active;
(III) Schiff base compounds containing 2-hydroxyphenyl methylene amino moiety bonded to a moiety which renders the compound capable of being a photochromic material; and
(IV) Schiff base compounds containing 4-hydroxyphenyl methylene amino moiety bonded to an unsubstituted or substituted 4-nitrophenyl moiety, wherein any substituent or substituents on the 4-nitrophenyl moiety, if any, is selected so that the Schiff base compound crystallizes in a non-centrosymmetric configuration.

18. A process for converting a fixed fundamental frequency of coherent laser light into a second harmonic frequency which comprises passing said laser light through a non-linear optical element comprising an organic molecular crystalline compound selected from the group consisting of wherein
R¹ represents a member selected from the group consisting of chloro, bromo, iodo, cyano, lower alkoxy, and lower alkylthio, and
R² represents a member selected from the group consisting of halo, cyano, lower alkoxy, lower alkylthio, and hydrogen, provided that R¹ is not the same as R²;

wherein
R³ represents a group which renders the molecule optically active, and
R⁴ represents a member selected from the group consisting of dimethylamino and diethylamino;

wherein
R⁵ represents a group which renders the molecule capable of being a photochromic material; and wherein $R^6$ represents a member selected from the group consisting of hydrogen, lower alkoxy, lower alkyl lower alkylthio, cyano, and halo, said compound being transparent to said fixed fundamental frequency and to said second harmonic frequency.

19. The process of claim 18 wherein said compound is wherein

$R^1$ represents a member selected from the groups consisting of chloro, bromo, iodo, cyano, lower alkoxy, and lower alkylthio, and $R^2$ represents a member selected from the group consisting of halo, cyano, lower alkoxy, lower alkylthio, and hydrogen, provided that $R^1$ is not the same as $R^2$.

20. The process of claim 19 wherein said compound is 2-[{(4-dimethylaminophenyl)methylene}amino]-4-chloro-methoxybenzene.

21. The process of claim 19 wherein said compound is 2-[{(4-dimethylaminophenyl)methylene}amino]-4-bromo-methoxybenzene.

22. The process of claim 18 wherein said compound is wherein

$R^3$ represents a group which renders the molecule optically active, and $R^4$ represents a member selected from the group consisting of dimethylamino and diethylamino.

23. The process of claim 22 wherein said compound is R-1-[{(4-diethylaminophenyl)methylene}amino]-1-phenylethane.

24. The process of claim 22 wherein said compound is S-1-[{(4-diethylaminophenyl)methylene}amino]-1-phenylethane.

25. The process of claim 18 wherein said compound is wherein $R^5$ represents a group which renders the molecule capable of being a photochromic material.

26. The process of claim 24 wherein said compound is [{(2-hydroxyphenyl)methylene]amino]benzene.

27. The process of claim 18 wherein said compound is wherein $R^6$ represents a member selected from the group consisting of hydrogen, lower alkoxy, lower alkyl, lower alkylthio, cyano, and halo.

28. The process of claim 27 wherein said compound is 3-methoxy-4-[{(4-hydroxyphenyl)methylene}amino]nitrobenzene.

* * * * *

UNITED STATES PATENT AND TRADEMARK OFFICE
CERTIFICATE OF CORRECTION

PATENT NO. : 4,733,109

DATED : March 22, 1988

INVENTOR(S) : Michael C. Palazzotto

It is certified that error appears in the above-identified patent and that said Letters Patent is hereby corrected as shown below:

Col. 2, line 9, "introducin" should be --introducing--.

Col. 8, line 23, "of" should be added before --the--.

Signed and Sealed this

Twenty-third Day of August, 1988

*Attest:*

DONALD J. QUIGG

*Attesting Officer*      *Commissioner of Patents and Trademarks*